United States Patent

Welker

Patent Number: 5,936,168
Date of Patent: Aug. 10, 1999

[54] DUAL INJECTOR CYLINDER AUTOMATIC INSERTION DEVICE FOR USE WITH HIGH PRESSURE PIPELINES

[76] Inventor: Robert H. Welker, P.O. Box 1406, Sugarland, Tex. 77487

[21] Appl. No.: 08/425,261

[22] Filed: Apr. 18, 1995

Related U.S. Application Data

[63] Continuation of application No. 08/136,374, Oct. 15, 1993, abandoned.

[51] Int. Cl.⁶ .................................................... G01N 3/00
[52] U.S. Cl. ........................................................... 73/866.5
[58] Field of Search ........................ 73/86, 863.5, 863.82, 73/863.85, 866.5

[56] References Cited

U.S. PATENT DOCUMENTS

| | | |
|---|---|---|
| 3,174,332 | 3/1965 | Echtler, Jr. et al. ................. 73/863.85 |
| 4,177,676 | 12/1979 | Welker . |
| 4,346,611 | 8/1982 | Welker . |
| 4,387,592 | 6/1983 | Welker . |
| 4,631,967 | 12/1986 | Welker . |
| 4,697,465 | 10/1987 | Evans et al. ............................ 73/866.5 |
| 4,841,787 | 6/1989 | Waterman ............................... 73/866.5 |
| 5,009,113 | 4/1991 | Kamrat ................................... 73/866.5 |
| 5,138,755 | 8/1992 | Evans et al. ........................... 73/866.5 |

*Primary Examiner*—Max H. Noori
*Attorney, Agent, or Firm*—Gunn & Associates, P.C.

[57] ABSTRACT

The present disclosure sets forths a pipeline insertion mechanism. It cooperates with the pipeline having a tee, blocking valve and stuffing box. An elongate insertion rod is extended from the exterior through the stuffing box, blocking valve and tee so that a measuring instrument is positioned at a centerline location in the pipeline. This rod connects to a transverse yoke having two ends which connects at the remote ends to piston rods. Two piston rods cooperative with two hydraulically cylinders are positioned adjacent to the blocking valve and stuffing block to reduce height of the equipment. The insertion rod is moved axially to insert or retract the measuring instrument.

11 Claims, 3 Drawing Sheets

DUAL INJECTOR CYLINDER AUTOMATIC INSERTION DEVICE FOR USE WITH HIGH PRESSURE PIPELINES

This application is a continuation of application Ser. No. 08/136,374, filed Oct. 15, 1993 now abandoned.

BACKGROUND OF THE DISCLOSURE

An insertion device is a device which is used to insert a measuring instrument or sensor into a pipeline. More particularly, a pipeline sampling device or flow meter is best operated at an axially aligned position in a pipeline. When the device is at the centerline axis of the pipeline, more accurate measurements are made. Some devices are installed in the pipe at an eccentric position. Such devices need occasional cleaning. This is true both for flow meters and product sampling devices. Regarding insertion of such measuring instruments, they must be periodically retracted.

Retraction is required to enable pipeline pigs to pass along the pipeline. Otherwise, a full gauge pipeline pig will bend the mounting mechanism, perhaps destroying the measuring instrument and at least positioning it at the wrong location. Even worse, the pipeline pig may snag on the measuring instrument, blocking the pipeline against flow and creating an undesired pressure increase behind the pipeline pig. For these reasons, the insertion device must operate periodically to retract the measuring instrument so that a pig can traverse the pipeline without damaging the pipeline.

The normal insertion device involves a long piston rod. Typically, a piston placed in a hydraulic cylinder provides power to force the rod (which supports the measuring instrument) into the pipeline. Since pipeline pressure can be several hundred psi, even when the rod has a cross-sectional area of only one square inch, the opposing force can be substantial. With that representative dimension, it requires 1000 lbs. of force to overcome an ambient pipeline pressure of 1000 psi. Adding in the frictional engagement of the stuffing box, the force can easily be substantial to insert the rod into the pipeline. Moreover the piston rod normally in the cylinder is part of the rod. The cylinder may have substantial length. When the cylinder is long and the pipeline diameter is fairly large, the piston rod has to be quite long also. This rod is loaded with the compressive or axial load from the operation of the hydraulically powered piston. Loading of the rod at the pipeline is substantially equal and opposite in direction. Therefore the rod has a tendency to flex or bend. This can be countered by making a larger diameter rod. In turn, however, that increases the weight of the rod and further creates problems with heavier equipment. The present disclosure is a system which is much better than the end loaded, axially aligned hydraulic cylinders used heretofore. Representative devices known in the prior art are shown by patents of the present inventor which includes U.S. Pat. Nos. 4,177,676; 4,387,592; 4,346,611 and 4,631,967.

The present structure is an apparatus which provides an improved insertion device construction. More particularly, it is able to power the insertion rod without extending the height of the structure. So to speak, this invention provides a folded structure. The folded structure assures the positioning of the power cylinder parallel and adjacent to the insertion rod. Rather than being axially aligned, the insertion rod is adjacent to the insertion cylinder. This creates the risk of twisting when power is applied by the hydraulic cylinder to the insertion rod. Therefore two insertion cylinders are utilized, the two bracketing the insertion rod. So to speak, duplicate left and right hydraulic cylinders operated with a common power source and operated in a common fashion provide the power stroke. They connect with a transverse yoke member which is constructed so that the pulling forces of the two insertion cylinders are arranged symmetrically to the left and right, thereby balancing and assuring smooth insertion. Moreover, the two cylinders are positioned immediately adjacent to the valve mechanism which connects laterally from the pipeline so that the assembled apparatus including the insertion rod is reduced in height. This provides a much shorter structure which reduces overhead clearance problems.

The main insertion rod is inserted by a transverse yoke mechanism connected with two hydraulically powered cylinders. A lock down collar cooperative with the yoke mechanism enables adjustment so that the rod is fixed in position. This enables proper orientation of the insertion rod and equipment mounted at the remote extremity of it.

Consider representative dimension for the present system. It may be necessary to install a tee in a pipeline with a laterally directed passage extending to a blocking ball valve. The ball valve is constructed in a housing terminating in a pair of spaced, parallel flanges for easy mounting. A stuffing box is attached at one end of the ball valve and the opposite end of the ball valve is connected to the tee. The stuffing box supports the seals which enables the rod to be inserted through the stuffing box, through the ball valve, through the tee and ultimately to position a measuring apparatus at a centerline location within the pipeline. This is accomplished by mounting the measuring equipment on the axially moveable insertion rod. The rod is normally aligned with and serial extended by an upstanding hydraulic cylinder. Collectively, all of the above described equipment arranged in serially fashion typically requires a very high ceiling to shelter the apparatus in a suitable housing or other enclosure.

The hydraulic cylinder appended to the end of the insertion rod is not utilized in this novel arrangement. Rather, the entire structure is shortened. It is shortened so that the hydraulic cylinder is positioned to the side, reducing the height of the structure, and balancing the forces applied to the rod. This is accomplished by utilizing a single supply system cooperative with duplicate, double, acting hydraulic cylinders which are extended in parallel and retracted in parallel. Moreover, the parallel connected insertion and retraction system is capable of retracting by creating the properly sized force to insert the rod against the ambient pressure existing in the pipeline. One advantage of the present apparatus is that the total height of the structure is markedly reduced. Height reduction is achieved through a folded mechanism so that duplicate hydraulic cylinders are positioned parallel to and offset from the insertion rod, and are located so that the parallel hydraulic cylinders are on the left and right of the insertion rod. The insertion rod can be selectively locked in place. This is accomplished by incorporating a lock down collar on the rod which is anchored, thereby permitting locking against further axially movement of the insertion rod. Rotational movement is adjusted, and thereafter end by locking the insertion rod at a particular angular orientation.

DESCRIPTION OF THE DRAWINGS

FIG. 2 is a view similar to FIG. 1 showing the insertion rod extended into the pipeline whereas FIG. 1 shows the rod retracted from the pipeline;

DETAILED DESCRIPTION

Figure 1:
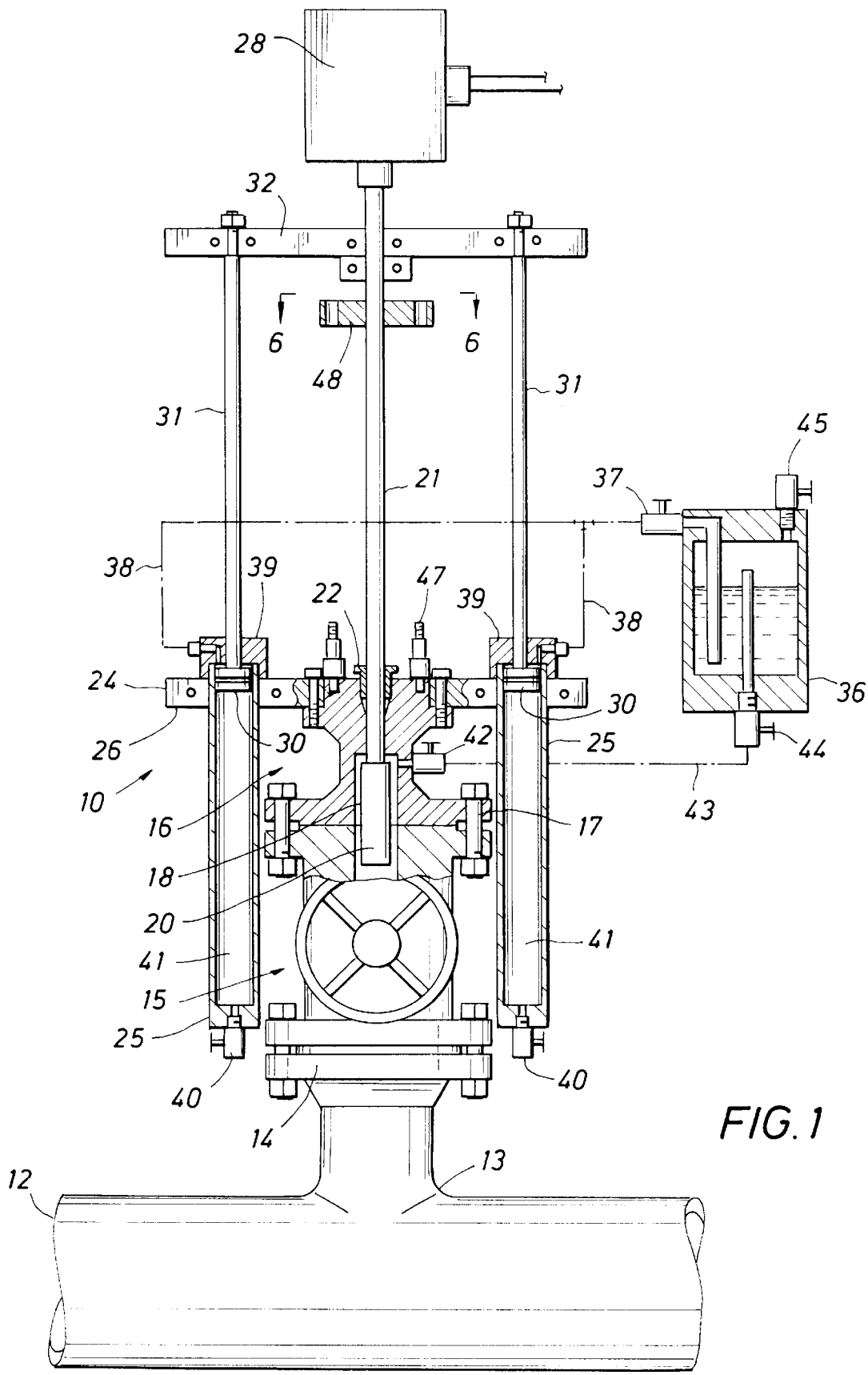
FIG. 1 is a side view of the apparatus of the present disclosure, showing a portion of the apparatus in sectional view, and illustrating left and right duplicate hydraulic cylinders for extension and retraction of an insertion rod into a pipeline.
Figure 2:
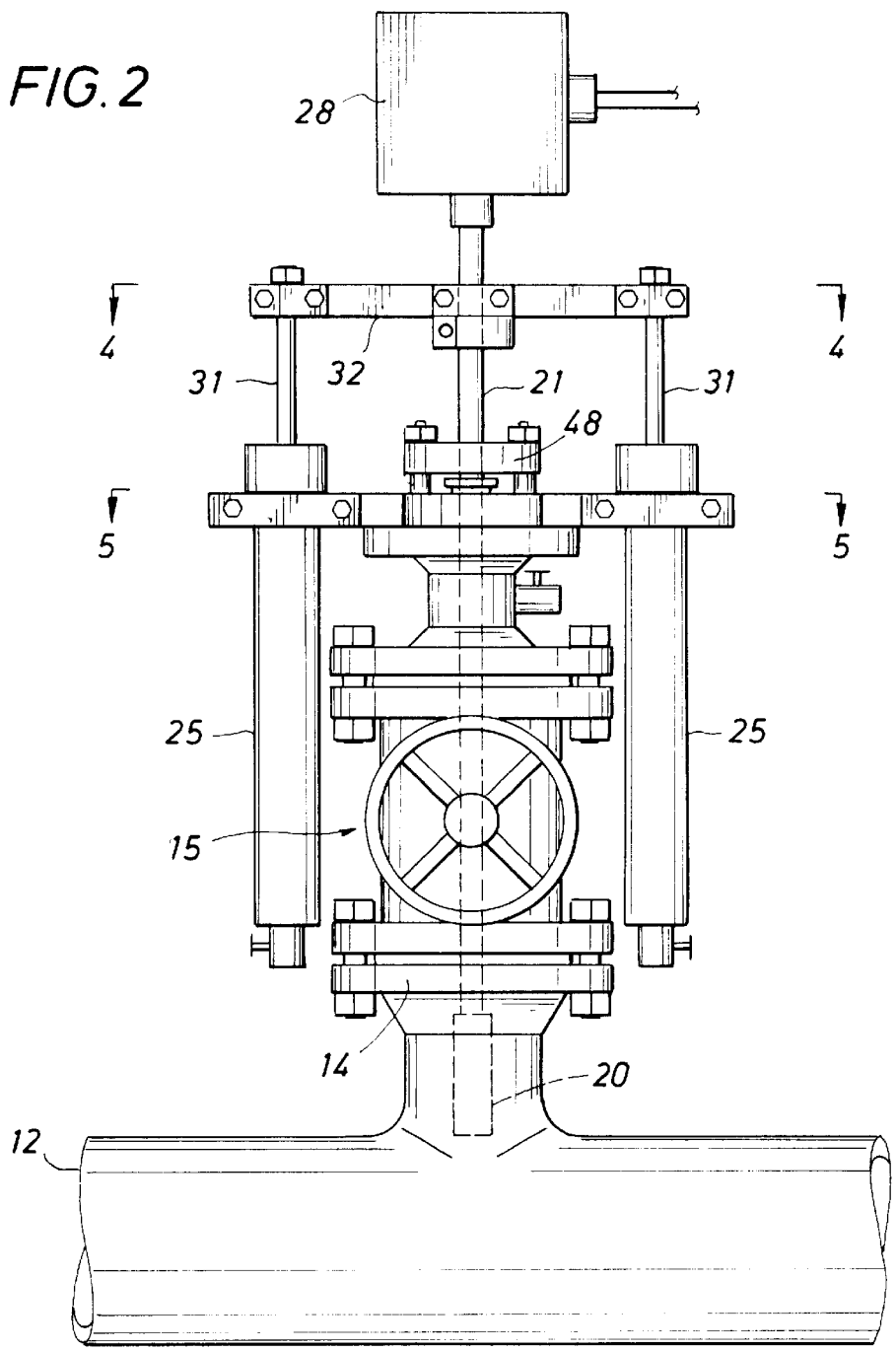

Attention is first direction to FIG. 1 of the drawings where the numeral 10 indicates the insertion apparatus of the present disclosure, speaking very generally. It is mounted for cooperation with a pipeline 12 which has an integrally constructed tee 13. The tee, whether welded or of flanged construction, turns at a right angle, thereby locating a point of entry. The tee defines the location at which a measuring instrument (to be described) is inserted into the pipeline. More particularly, the tee 13 terminates at a flange 14 to enable easy attachment of a valve assembly 15. The valve assembly 15 is incorporated so that flow through the tee can be interrupted. The valve normally has two operative conditions which are fully opened or fully closed. When fully open, the valve defines a passage into the tee 13 so that the measuring device to be described can be inserted into the pipeline 12. More particularly, the tee is constructed so that the laterally extending tee can be positioned at a particular angular orientation. It is preferable that it be an upstanding structure. This enables the use of overhead hoist equipment and the like to install the valve on the pipeline, to manipulate the necessary equipment for insertion through the valve, and to also permit overhead support during repair or refurbishment. It is however possible that the tee can be angularly positioned so that it extends horizontally. In either event, the tee is incorporated so that easy entry into the pipeline can be obtained without leakage of pipeline product.

The valve 15 is constructed with an external valve body which terminates in a pair spaced flanges. The uppermost flange enables connection with a stuffing assembly 16. The stuffing assembly 16 incorporates a matching flange 17. The flange 17 is incorporated so that it matches the flange of the valve, thereby permitting connection with nuts and bolts which are attached in accordance with an industry standard. Moreover, the stuffing assembly 16 incorporates an axial passage which terminates at an enlarged chamber 18, the chamber being provided for recessing and thereby sheltering an instrument 20 which is inserted on the end of an insertion rod 21. The rod 21 passes through a suitable hollow nut 22 which cooperates with one or more seal rings captured below the nut 22 so that the several seal rings seal against the insertion rod when tightened by the nut 22. Moreover, this provides a pressure seal assembly so that leakage does not occur along the rod 21.

The stuffing assembly 16 incorporates a set of bolt openings arranged in a circle about the stuffing assembly. This enables a transverse lower yoke 24 to be attached. The yoke 24 better shown in FIG. 5 of the drawings, aligned by bolts with the stuffing assembly 16. In addition to that the yoke 24 includes outwardly extending arms which incorporate aligned bolt openings so that upstanding hydraulic cylinders 25 (see FIG. 1) are clamped by the notched bars 26 shown in FIG. 5 of the drawings. The bottom yoke assures alignment of twin hydraulic cylinders on the left and right as will be detailed.

Returning again to the aligned assembly of the tee 13, the valve 15, the stuffing assembly 16, it will be observed that the insertion rod 21 has sufficient length to insert the instrument 20 through and into the pipe 12. It is inserted to a centerline position. The measuring instrument 20 is typically a device which extracts a sample which is delivered outwardly along the insertion rod 21. In an alternate aspect, it is a measuring device such as a turbine flow meter. In either case, the instrument 20 makes the measurements as mentioned. More importantly, the measuring instrument is located at the proper position to be registered, thereafter being left at that position for an indefinite interval. Since the rod 21 has sufficient length to enable the instrument 20 to move from the recessed retracted position shown in FIG. 1 of the drawings, it is a fairly long rod. As desired, the rod 21 extends upwardly to a junction box 28 to enable connection with circuitry appropriate for the measuring instrument. For instance, if the measuring instrument is a turbine flow meter, the output is normally a procession of pulses. The junction box 28 enables the signal conductors to deliver the pulsed output so that the pulse singal can be used elsewhere in the system.

The present apparatus is constructed so that the rod is inserted through the stuffing box. The rod must work against a pressure head which is dependent on pressure in the pipeline. The rod can be isolated by closing the valve 15, when the valve is opened, the rod is exposed to the ambient or prevailing pressure in the pipeline. It is not uncommon to utilize pressure as high as 2000 psi in the pipeline. In that instance, the prevailing pipeline pressure acts against the rod to force the rod out of the system. If the rod has a cross-sectional area of one square inch, then the representative pipeline pressure 2000 psi will provide a force of 2000 lbs. attempting to expel the rod. This must be overcome by a force of at least 2000 lbs. to insert the rod, thereby moving the test instrument 20 to the desired location. To accomplish this, the applied force must actually be greater because there are additional forces involved in operation. For instance, there is a frictional drag at the seal rings. In this example, it is not uncommon to require about 2200 lbs. of force to insert the rod against the back pressure given in the foregoing example.

Figure 4:
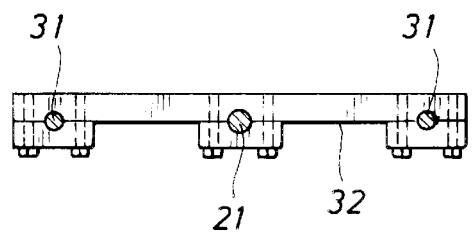
FIG. 4 is a sectional view taken along the line 4—4 of FIG. 2 of the drawing showing details of construction of the top yoke which connects with the insertion rod.

The present apparatus utilizes the twin or duplicate hydraulic cylinders 25 which are deployed on the left and right. Recall that they are locked in position by the yoke 24 better shown in FIG. 5 of the drawings. Moreover, each of the hydraulic cylinders incorporates a movable piston 30. The piston 30 connects with a piston rod 31, there being symmetrical piston rods on the left and right. The two piston rods 31 extend upwardly to the top yoke 32 which is also shown in FIG. 4 of the drawings. The yoke 32 clamps to the rod 21. Likewise, the piston rods 31 are connected to the top yoke 32 so there is no slippage. Accordingly, when the two piston rods are extended, they extend jointly and they retract jointly. This mode of operation is accomplished by operating the two hydraulic cylinders 25 with a common hydraulic system. More particularly, the numeral 36 identifies a hydraulic oil reservoir. It is provided with hydraulic oil which is delivered through a valve 37 connecting with duplicate flow lines. The flow lines from the valve 37 are identified in symbolic form at 38 and extend to the cylinder heads 39 closing the top of the left and right duplicate cylinders 25. The pistons are located below the cylinder heads 39 which are ported so that hydraulic pressure is introduced above the pistons 30, thereby forcing them downwardly. There is a chamber in each of the two duplicate cylinders located below the pistons 30. The lower chamber, identified by the numeral 41, is evacuated to atmosphere through a bleed valve 40 incorporated for this purpose. The bleed valve can conveniently be connected into the hydraulic system to provide pressure to it should this be required. However, there is another source of pressure which effectively makes the two hydraulic systems double acting. The double acting aspect is obtained from hydraulic pressure occurring elsewhere. If desired, the bleed valves 40 can be used as the inputs into the chambers 41 to enforce extension of the piston rods 31.

As noted, the hydraulic system delivers hydraulic fluid under pressure. The hydraulic fluid is maintained at an elevated pressure. Ordinarily, the pipeline is used to deliver flowing natural gas. Ambient pipeline pressure is observed in the pipeline, also in the valve 15, and in the stuffing assembly 16. A control valve 42 connects to the stuffing assembly 16 at a location to remove high pressure gas from the pipeline. The valve 42 is connected through a line 43 to a off/on control valve 44 and then to the pressure chamber 36. It is desirable that the pressure chamber be partly filled, thereby leaving room for a gas cushion above the hydraulic oil The gas introduced from the pipeline into the hydraulic chamber forms a cushion overhead so that the pressure on the hydraulic system is substantially equal to the pressure in the pipeline. Thus, if the pipeline pressure is 100 psi, then the pressure on the hydraulic system is about 100 psi. If the pipeline pressure is 2000 psi, then the same pressure is introduced into the hydraulic system and the hydraulic oil is pressurized to the same level. In the event of oil loss, an oil fill port 45 is likewise included. Oil filling can occur after closing the valve 44. This valve separates the hydraulic system from the pipeline pressure so that service can be carried out.

Figures 3, 5, 6:
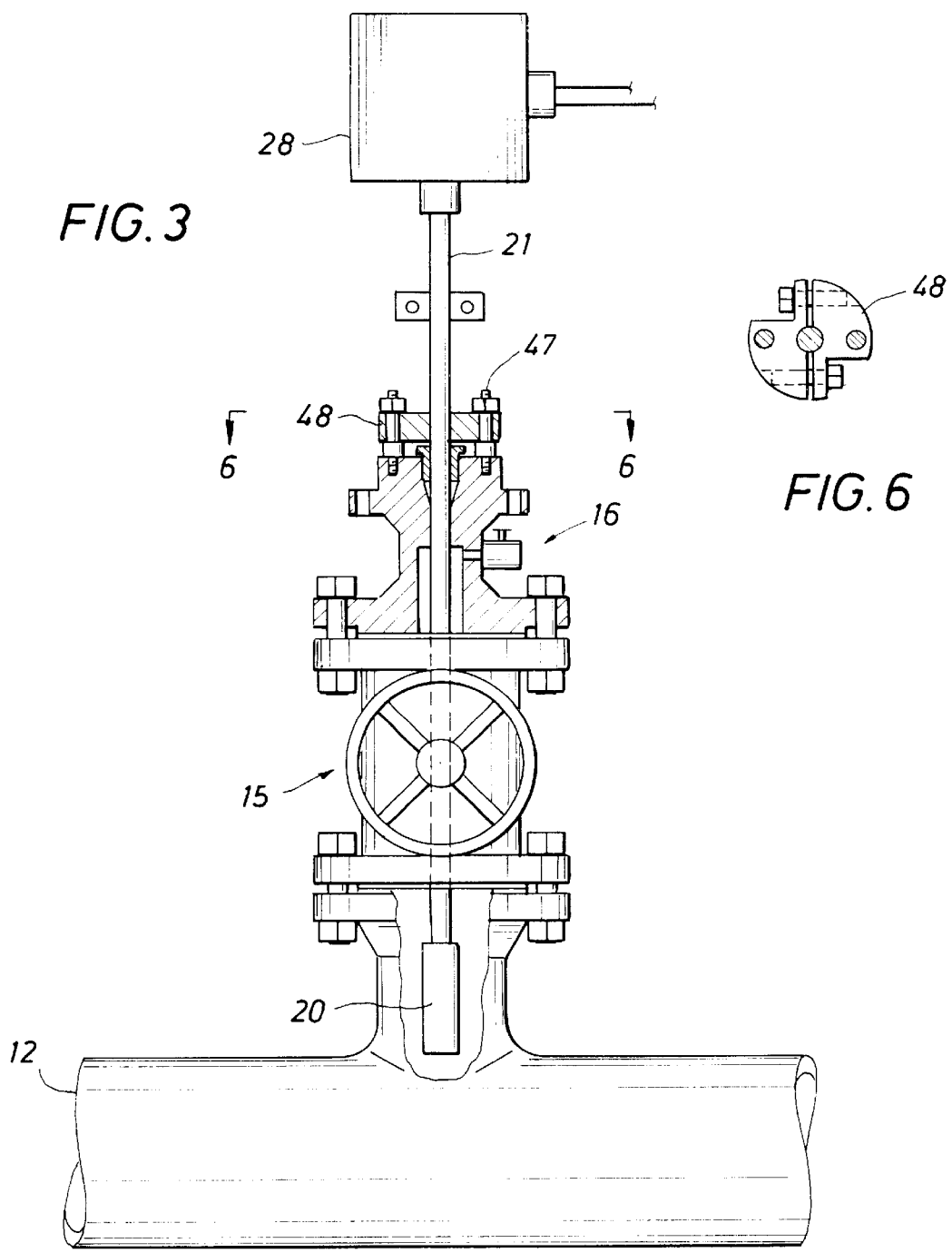
FIG. 3 is a view similar to FIGS. 1 and 2 which shows the insertion rod after removal of the hydraulic apparatus for insertion of the rod into the pipeline.
FIG. 5 is a sectional view taken along the line 5—5 of FIG. 2 of the drawings showing details of the bottom yoke construction.
FIG. 6 is a sectional line taken along the line 6—6 in FIG. 1 of the drawings showing details of construction of a lock collar on the insertion rod.

More particularly, the flow of gas at pipeline pressure into the hydraulic system assures that the hydraulic system is able to provide an adequate force. In that particular instance, and recalling the example given above where 2200 lbs. of force is required to insert the rod 21, the two cylinders are sized so that the pistons 30 have an adequate cross-sectional area to create such a force. Perhaps this will become more evident in describing a cycle of operation. One of the main aspects of the present system to be noted, and an important aspect at that, is the ability of the system to lock in place, thereby assuring that the test instrument is at the required location. The stuffing assembly 16 incorporates a pair of upstanding bolts 47. There is a lock collar 48 anchored to the insertion rod 21. The collar 48, being shown in FIG. 6 of the drawings, is clamped and secured at a particular angular orientation with respect to the rod. As shown in FIG. 6 of the drawings, the lock collar can rotate around the rod. Through the use of suitable bolts (not shown), the two halves of the lock collar are pulled together and fastened snuggly around the rod 21. This enables the rod to be fixed so that the measuring instrument 20 is installed at the right depth with respect to the axis of the pipeline. A flow meter of the sort normally placed in the pipeline must be aligned with the centerline axis for best operation. More specifically, the flow meter must be aligned so that the flow meter is able to intercept the axial flow through the pipeline. It is not desirable that the flow meter be positioned at any other angle. This requires that the flow meter the aligned with the respect to the rod. The preferred angular orientation of the flow meter must likewise be incorporated in the angular orientation of the rod 21. The rod 21 is able to be inserted at any angular rotation because it is round. It is preferably marked with a paint mark or other mark on the exterior surface indicating the angular position of the measuring instrument 20. More importantly, this is exposed on the exterior so that the rod can be rotated and positioned as required. The rod is rotated to assure proper orientation of the measuring instrument 20. Once it is rotated, the collar 48 is loosened pull down to the protruding bolts 47, and then aligned with those bolts, and the collar is then locked in place. This assures that the collar engaged with the bolts 47 moves the measuring instrument 20 to the required angular position.

When the equipment is installed on a pressurized pipeline as shown in FIG. 1 of the drawings, hydraulic pressure is raised by first opening the metering valve 42 and the valve 44. This delivers gas under pressure into the hydraulic system. Once the pressure in the chamber 36 equals the pressure in the pipeline, the system is then ready to operate. The valve 37 is opened to deliver hydraulic oil. The oil under pressure acts on the two pistons 30 forcing them downwardly against a common back pressure. Both of the bleed valves 40 are opened to evacuate the back side chambers 41. The piston rods 31 are retracted identically. Furthermore, the top yoke is pulled downwardly. Since it is clamped (see FIG. 4) to the rod 21, the rod 21 is forced downwardly. As will be understood, the rod 21 is made of sufficient length so that the measuring instrument 20 is inserted to the desired central location in the pipeline 12. Once that position is achieved, the lock collar 48 can then be locked into position. Initially downward yoke movement occurs with the bolts 47 extending upwardly devoid of nuts. This enables the lock collar to travel downwardly until it is positioned over the bolts 47. Then, fastening can be accomplished. At this point, the rod 21 is held at the inserted position. Nothing further is required to sustain that position. Hydraulic power necessary for insertion is no longer needed. Rather, the hydraulic system can be switched off or even removed. At this juncture, the insertion rod 21 is fully clamped and cannot move and will not retract the measuring instrument 20.

Going now to FIG. 3 of the drawings, this shows how the equipment can be retracted. Briefly, the collar 48 can be loosened. As illustrated in FIG. 6 of the drawings, it incorporates receptacles for two bolts to clamp on the rod 21. These can be loosened which will then permit the rod 21 to be pumped out the system. Recall that the rod 21, having a defined crosssectional area, is exposed to prevailing pipeline pressure. That pressure will create a force of about 2000 lbs. in the example given above to force the rod 21 out of the pipeline. This will permit the rod to traverse the equipment, thereby pulling the measurement instrument 20 to the receptacle above 15. At that point, the valve 15 can be operated to close the stuffing assembly 16, isolating it from pipeline pressure. Thus, the measuring device can be easily retracted from the operative position which is achieved within the pipeline.

Benefits of the Device

The dual acting hydraulic system shown in the foregoing disclosure is highly efficient. It requires no independent pressure source, being driven by prevailing pipeline pressure. Just as importantly, it is not aligned with the rod 21. The rod is loaded in an entirely different fashion. In this instance, the hydraulic cylinders are substantially shorter in height by repositioning to the side of the blocking valve 15. This reduces the overhead structure which is required to clear the equipment. The building which houses this equipment can be exceedingly tall depending on the length of stroke and scale factors of the equipment. The structural height is substantially reduced. For instance, if the stroke of the rod is four feet, then the rod sometimes extends above the stuffing assembly by four feet. However, the length is not further extended by the hydraulic cylinder which must, of necessity, be at least four feet in length to accomplish a four foot stroke. In this particular, if the required stroke is four feet, the hydraulic cylinders 25 will typically have a length of nearly five feet. But it is not additive to the height, thereby reducing, or even avoiding overhead clearance problems.

On careful review of the drawings of the present disclosure, it will be observed that the rod 21 must recipocate, periodically in anticipation of passage of a pipeline pig. Through the use of appropriate up line pig passage detectors, a signal can be provided to an electrically controlled valve. For instance, it is possible to close the valve 44 while opening the valve 45. This will vent the gas cushion in the pressure chamber 36 to atmosphere, thereby reducing the pressure on the hydraulic oil. That will drop the pressure above the duplicate pistons 30. Prevailing line pressure in the pipe 12 will then force the measuring instrument 20 upwardly because the insertion rod 21 is forced to the retracted position shown in FIG. 1 of the drawings. This movement obviously requires that the lock collar 48 be unbolted from the bolt 47. Retraction occurs and the pig can pass safely without bending the insertion rod or damaging the sensor attached to it. Indeed, the rod 21 is retracted by the pressure differential acting on the rod. While one end of the rod is exposed to pipeline pressure, the opposite end is exposed to a reduced pressure and the differential in pressure forces the rod upwardly through the stuffing assembly 16. Chance rotation of the rod 21 normally does not occur, but if there is any measure of concern, the alignment bolts 47 can simply be extended in length. One feature of the present apparatus is the retraction of the sensor so that it is pulled to the side while yet permitting the pig to pass safely through the pipeline. Later, the operative conditions of the valves 44 and 45 can be changed by closing the valve 45 and opening the valve 44. This will restore the required pressure to the chamber 36 so that the pressurized gas cushion above the hydraulic oil restores the necessary operating pressure to the system. When the pressure in the chamber 36 is sufficient, hydraulic oil is again forced through the flow lines 38 to the top side of the two duplicate pistons 30 and the piston rods 31 are retracted, pulling the insertion rod downwardly. This will then reposition the measuring instrument in the pipeline 12 at the required location. The actual range of travel can be limited by mounting the lock collar at the required location to limit such travel. Once the sensor has been restored to the required position, data output from the sensor is delivered to cooperative circuitry elsewhere by connecting the output signal from the sensor 20 through the rod 21, junction box 28, and then to suitable electrical conductors extending elsewhere.

While the foregoing is directed to the preferred embodiment, the scope is determined by the claims which follow:

What is claimed is:

1. A method of inserting a measuring instrument into the central portions of a pipeline to thereby measure aspects of fluid flow through the pipeline, and including the steps of:
   (a) positioning a measuring instrument on an end of an insertion rod;
   (b) positioning the insertion rod through a stuffing assembly so that the end thereof is moveable into or away from the interior of the pipeline;
   (c) applying a force to a second end of said rod wherein the second end is on the exterior of the pipeline so that the second end is forced toward the pipeline to achieve insertion into the pipeline;
   (d) utilizing line pressure to form a pressurized fluid applied to a motive means to thereby force movement of said rod; and
   (e) wherein the step of applying a force to the second end of said rod is accomplished laterally of said rod which precludes extending beyond said rod.

2. The method of claim 1 wherein the step of applying a force to the second end occurs to the side of said rod to limit structural extension beyond said rod.

3. The method of claim 1 including the preliminary step of positioning the insertion rod so that it moves in a linear direction into and out of the interior of the pipeline along a pathway of movement of linear movement;
   (a) wherein the step of applying the force to the second end of that rod is accomplished laterally of said rod to the side of said rod; and
   (b) wherein the step of applying the force is accomplished by laterally displaced cylinders having pistons therein and wherein said laterally displaced cylinders and pistons therein move extending piston rods connected to a laterally disposed, transverse member connected to said rod to thereby move said rod in linear movement.

4. A pipeline insertion apparatus for making measurements of conditions in a pipeline by inserting a measuring mechanism through a stuffing assembly and blocking valve extending outwardly from and in communication with the pipeline and positioning the measuring mechanism at a desired location within the cross sectional area of the pipeline, the apparatus comprising:
   (a) a laterally extending mounting member fixedly attached to the stuffing assembly and blocking valve, the mounting member having two opposing ends;
   b) an elongate insertion rod in sliding engagement relative to said laterally extending mounting member having a measuring end and a distal end, the insertion rod being axially aligned for insertion of the measuring end into the pipeline through said extending mounting member, the stuffing assembly, and the blocking valve, wherein the measuring end is capable of supporting a measuring mechanism;
   (c) a laterally extending yoke connected with the distal end of the insertion rod having two opposing ends aligned with the opposing ends of said mounting member;
   (d) a pair of parallel hydraulic cylinders, each hydraulic cylinder having an elongate cylinder body extending toward the pipeline adjacent to and aligned at the side of the stuffing assembly and blocking valve, a piston movably located in each of said cylinders, and a piston rod extending from said piston for connection to relatively move said yoke with respect to said mounting member wherein the pipeline insertion apparatus extends from the pipeline parallel to the insertion rod, and wherein the application of pressurized fluid to the piston moves the piston rod to move said yoke towards or away from the pipeline to insert or retract the measuring end of the insertion rod into the pipeline wherein the pair of hydraulic cylinders operate jointly in response to a common pressurized fluid system to provide movement of the rod without bending from said pair of cylinders to the side of the stuffing assembly.

5. The apparatus of claim 4 wherein said cylinders are located on the left and right and are jointly operative and are connected with said yoke and said yoke extends symmetrically left and right for connection so that said rod is forced into the pipeline through said stuffing assembly, blocking valve and pipeline against pressure prevailing in the pipeline which would otherwise force said rod out of the pipeline.

6. The apparatus of claim 4 wherein said cylinders are parallel and spaced on opposite sides of the stuffing assembly.

7. The apparatus of claim 4 wherein said hydraulic cylinders enclose upper and lower chambers divided by said pistons, and said upper chamber is beneath a head of said cylinder to enable hydraulic oil introduced into said chamber to retract said piston rods and thereby impart insertion movement to said rod.

8. A pipeline insertion apparatus for making measurements of conditions in a pipeline by inserting a measuring mechanism through a stuffing assembly and blocking valve extending outwardly from and in communication with the pipeline and positioning the measuring mechanism at a desired location within the cross sectional area of the pipeline, the apparatus comprising:

(a) a laterally extending mounting member fixedly attached to the stuffing assembly and blocking valve, the mounting member having two opposing ends;

b) an elongate insertion rod in sliding engagement relative to said laterally extending mounting member having a measuring end and a distal end, the insertion rod being axially aligned for insertion of the measuring end into the pipeline through said extending mounting member, the stuffing assembly, and the blocking valve, wherein the measuring end is capable of supporting a measuring mechanism;

(c) a laterally extending yoke connected with the distal end of the insertion rod having two opposing ends aligned with the opposing ends of said mounting member;

(d) a pair of parallel hydraulic cylinders, each hydraulic cylinder having an elongate cylinder body extending toward the pipeline adjacent to and offset to the side of the stuffing assembly and blocking valve, a piston movably located in each of said cylinders, and a piston rod extending from said piston for connection to relatively move said yoke with respect to said mounting member wherein the pipeline insertion apparatus extends from the pipeline to operate the insertion rod, and a common pressurized fluid source applies pressure to the piston to move the piston rod and move said yoke towards or away from the pipeline to insert or retract the measuring end of the insertion rod into the pipeline wherein the pair of hydraulic cylinders operate jointly in response to said common pressurized fluid source to cause movement of the rod without bending from said pair of cylinders to the side of the stuffing assembly.

9. The apparatus of claim 8 wherein said cylinders are located on the left and right and are jointly operative and are connected with said yoke and said yoke extends symmetrically left and right for connection so that said rod is forced into the pipeline through said stuffing assembly, blocking valve and pipeline against pressure prevailing in the pipeline which would otherwise force said rod out of the pipeline.

10. The apparatus of claim 8 wherein said cylinders are parallel and spaced on opposite sides of the stuffing assembly.

11. The apparatus of claim 8 wherein said hydraulic cylinders enclose upper and lower chambers divided by said pistons, and said upper chamber is beneath a head of said cylinder to enable hydraulic oil introduced into said chamber to retract said piston rods and thereby impart insertion movement to said rod.

* * * * *